United States Patent
Sergienko et al.

(10) Patent No.: US 6,822,739 B2
(45) Date of Patent: Nov. 23, 2004

(54) ENTANGLED-PHOTON ELLIPSOMETRY

(75) Inventors: Alexander V. Sergienko, Boston, MA (US); Bahaa E. A. Saleh, Lexington, MA (US); Malvin C. Teich, Boston, MA (US); Kimani C. Toussaint, Jr., Brookline, MA (US); Ayman F. Abouraddy, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 10/441,889

(22) Filed: May 20, 2003

(65) Prior Publication Data

US 2004/0036877 A1 Feb. 26, 2004

Related U.S. Application Data

(63) Continuation of application No. PCT/US01/43713, filed on Nov. 21, 2001.
(60) Provisional application No. 60/252,846, filed on Nov. 22, 2000, and provisional application No. 60/310,901, filed on Aug. 8, 2001.

(51) Int. Cl.$^7$ ................................................ G01J 4/00
(52) U.S. Cl. ...................................... 356/369; 356/368
(58) Field of Search ................................ 356/370, 368, 356/369, 364, 365, 366, 367; 372/21, 27; 250/225

(56) References Cited

U.S. PATENT DOCUMENTS

| | | | |
|---|---|---|---|
| 5,548,404 A | | 8/1996 | Kupershmidt et al. |
| 5,796,477 A | * | 8/1998 | Teich et al. .................. 356/318 |
| 6,424,665 B1 | * | 7/2002 | Kwiat et al. ................... 372/21 |
| 6,556,306 B2 | * | 4/2003 | Jiang et al. ................... 356/517 |
| 6,567,164 B2 | * | 5/2003 | Birk et al. .................... 356/317 |
| 6,646,727 B2 | * | 11/2003 | Saleh et al. ................. 356/73.1 |

OTHER PUBLICATIONS

"Ellipsometric measurements by use of photon pairs generated by spontaneous parametric downconversion"; Abouraddy et al., Nov. 1, 2001, vol. 26, No. 21, Optical Society of America; pp. 1717–1719.

"Entangled–photon ellipsometry"; Abouraddy et al., Journal Optical Society of America; vol. 19, No. 4; Apr. 2002; pp. 656–662.

* cited by examiner

*Primary Examiner*—Gregory J. Toatley, Jr.
*Assistant Examiner*—Layla Lauchman
(74) *Attorney, Agent, or Firm*—Gauthier & Connors LLP

(57) ABSTRACT

A system for obtaining ellipsometric data from a sample. The system includes a source for providing a monochromatic light beam. The system also includes a nonlinear crystal for converting the monochromatic light beam into photon pairs by disintegrating photons from the monochromatic light beam, such that each of the photon pairs exhibits entanglement properties, wherein one of the photons of the pair is directed to the sample and the other of the photons of the pair is not directed to the sample. The system further includes a circuit for calculating the coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

67 Claims, 4 Drawing Sheets

ENTANGLED-PHOTON ELLIPSOMETRY

This is a continuation of PCT/US01/43713, filed Nov. 21, 2001.

This application claims priority from provisional applications Ser. Nos. 60/252,846 filed Nov. 22, 2000, and 60/310,901 filed Aug. 8, 2001.

SPONSORSHIP INFORMATION

This invention was made with Government Support under Contract Numbers EEC-9986821 and ECS-9810355 awarded by the National Science Foundation. The Government has certain rights in the invention.

BACKGROUND OF THE INVENTION

The invention relates to the field of quantum ellipsometry, which relies on the use of non-classical optical sources in conjunction with a coincidence-detection scheme. One of the age of old questions in the field has been: how does one measure reliably the reflection or transmission coefficient of an unknown sample? The reliability of these measurements heavily depend on the reliability of the source and detector used in the measurements. In the ideal condition, both the source and detector are absolutely calibrated. In practice, this condition is never met. However, high precision measurements are often required, thus, a multitude of experimental techniques have been developed. Two of those techniques, are the null and interferometric approach, allow getting around the imperfections of devices used in the measurements.

In the field of ellipsometry, high precision measurements are necessary in which the polarization of light is used to determine the properties of various optical samples. Ellipsometers have demonstrated to be useful also in other fields that require high precision measurement, such as biomedical applications.

In an ideal ellipsometer, the light emitted from a reliable optical source is directed into an unknown optical system (which may be an unknown sample that reflects the impinging light) and thence into a reliable detector. The practitioner keeps track of the emitted and detected radiation, and can infer information about the optical system. A device may be used as an ellipsometer if the source can emit light in any specified state of polarization. A sample is characterized by two parameters $\psi$ and $\Delta$. The quantity $\psi$ is related to the magnitude of the ratio of the sample's eigenpolarization complex reflection coefficients, $r_1$ and $r_2$, via $$\tan\psi = \left|\frac{\tilde{r}_1}{\tilde{r}_2}\right|;$$

$\Delta$ is the phase shift between them.

FIG. 1 illustrates the traditional null ellipsometer arrangement. A sample 7 is illuminated with a beam of light that is polarized by a linear polarizer 4 from a source 2. The reflected light from the sample 7 is generally elliptically polarized, is then analyzed. The polarization of the incident beam is adjusted by a linear polarization analyzer 6 for the change in the relative amplitude and phase, introduced by the sample, between the two eigenpolarization, such that the reflected beam is linearly polarized. Once the reflected beam passed through an orthogonal linear polarizer 6, the linearly polarized beam will yield a null measurement at the optical detector 8.

As stated above, the null ellipsometer does not require a calibrated detector since it does not measure intensity, but records a null. The principal drawback of null measurement techniques is the need for a reference to calibrate the null. For example, to define an initial location (the rotational axis of reference at which an initial null is obtained), and then to compare subsequent locations upon inserting the sample. Thus, eliminating the problem of an unreliable source and detector but necessitating the use of a reference sample. The accuracy and reliability of the measurement results depend on the information regarding the reference sample used. In this instant, the measurements are a function of $\psi$, $\Delta$, and other essential parameters of the reference sample.

The inteferometric ellipsometer requires a configuration in which light from the source follows more than one path, usually created by the aid of beam splitters before reaching a detector. A sample is placed on one of those paths. Thus, the efficiency of the detector can be measured by performing measurements when the sample is removed from the interferometer. The problem of an unreliable detector is eliminated, however, the reliability of the source and other components (beam splitters, mirrors, etc.) still remain. The accuracy of the measurements are limited by the information known regarding the parameters characterizing these optical components. The stability of the optical arrangement is also of importance to the performance of such a device.

SUMMARY OF THE INVENTION

Accordingly, the invention presents a novel interferometric technique to perform reliable ellipsometric measurements. This technique relies on the use of a non-classical optical source in conjunction with a coincidence-detection scheme. The ellipsometric measurements acquired with this scheme are absolute, and they neither require neither source nor detector calibration, nor do they require a reference.

According to one embodiment of the invention, a system for measuring ellipsometric data from a sample is provided. The system includes a source for providing a monochromatic light beam. The system also includes a nonlinear crystal for converting the monochromatic light beam into photon pairs by disintegrating photons from the monochromatic light beam, such that each of the photon pairs exhibits entanglement properties, wherein one of the photons of the pair is directed to the sample and the other of the photons of the pair is not directed to the sample. The system further includes a circuit for calculating the coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

According to another aspect of the invention, a method of measuring ellipsometric data from a sample is provided. The method includes providing a monochromatic light beam, and converting the monochromatic light beam into photon pairs by disintegrating photons from the monochromatic light beam, such that each of the photon pairs exhibits entanglement properties, wherein one of the photons of the pair is directed to the sample and the other of the photons of the pair is not directed to the sample. The method further comprises calculating the coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

According to another aspect of the invention, a system for measuring ellipsometric data from a sample is provided. The system includes a source for providing a monochromatic light beam, and a nonlinear crystal for converting the monochromatic light beam into photon pairs and creating a first beam that includes photon-pairs from disintegrated photons from said monochromatic beam. The system further includes a first beam splitter for splitting the first beam into a second beam and third beam, wherein the second beam includes photons from the photon-pairs directed to the sample and the third beam includes photons from the photon-pairs not directed to the sample. The system also comprises a second beam splitter for combining reflected photons from the sample of the second beam and third beam into a recombined beam and splitting the recombined beam into a fourth and fifth beam. The system also includes a coincidence circuit for calculating the coincidence of the fourth and fifth beam, wherein measurements on the sample are obtained by analyzing the coincidence and entanglement properties of the photons in the fourth and fifth beam.

According to another aspect of the invention, a system for measuring ellipsometric data is provided. The system includes a source for providing a monochromatic light beam, and nonlinear crystal for converting the monochromatic light beam into photon pairs and creating a first beam that includes photon-pairs from disintegrated photons from said monochromatic beam. The system also includes a first beam splitter for splitting the first beam into a second and third beam, wherein the second beam includes photons from the photon-pairs directed to the sample and the third beam includes photons from the photon pairs not directed to the sample. The system further includes a coincidence circuit for calculating the coincidence of reflections from the sample of the second beam and third beam, wherein the measurements of the sample are obtained by analyzing the coincidence and properties of the photons pairs between the reflections from the sample of the second beam and third beam.

According to another aspect of the invention, a method of measuring ellipsometric data from a sample is provided. The method includes the steps of providing a monochromatic light beam, and converting the monochromatic light beam into photon pairs and creating a first beam that includes photon-pairs from disintegrated photons from said monochromatic beam. The method also includes step of splitting the first beam into a second and third beam, wherein the second beam includes photons from the photon-pairs directed to the sample and the third beam includes photons from the photon pairs not directed to the sample. The method further includes step of calculating the coincidence of reflections from the sample of the second beam and third beam, wherein the measurements of the sample are obtained by analyzing the coincidence and properties of the photons pairs between the reflections from the sample of the second beam and third beam.

According to another aspect of the invention, a method of measuring ellipsometric data from a sample is provided. The method includes providing a monochromatic light beam, and converting the monochromatic light beam into photon pairs and creating a first beam that includes photon-pairs from disintegrated photons from said monochromatic beam. The method further includes splitting the first beam into a second beam and third beam, wherein the second beam includes photons from the photon-pairs directed to the sample and the third beam includes photons from the photon-pairs not directed to the sample. The method also comprises combining reflected photons from the sample of the second beam and third beam into a recombined beam and splitting the recombined beam into a fourth and fifth beam. The method also includes calculating the coincidence of the fourth and fifth beam, wherein measurements on the sample are obtained by analyzing the coincidence and entanglement properties of the photons in the fourth and fifth beam.

According to another aspect of the present invention, a system for measuring ellipsometric data from a sample is provided. The system includes an entangled photon-pair generator for converting a monochromatic light beam into photon pairs, such that one of the photons of the pair is directed to the sample and the other of the photons of the pair is not directed to the sample. The system also includes a coincidence measuring device for calculating the coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

According another aspect of the present invention, a method of measuring ellipsometric data from a sample is provided. The method a converting a monochromatic light beam into photon pairs, such that one of the photons of the pair is directed to the sample and the other of the photons of the pair is not directed to the sample. The method also includes calculating the coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

DETAILED DESCRIPTION OF THE INVENTION

The present invention provides a novel technique for obtaining reliable ellipsometric measurements based on the use of twin photons produced by the process of spontaneous optical parametric down conversion (SPDC). The present invention extends the use of non-classical light sources in ellipsometric measurements. The ellipsometric measurements acquired with the use of the present invention are absolute, they do not require that the source and detector be absolutely calibrated nor do they require a reference.

Several of the embodiments of the present invention utilize entangled-photon quantum ellipsometry to obtain high accuracy in ellipsometric measurements. This eliminates the need to be dependent on the optical components in the system. Thus, the various embodiments illustrate utilizing entangled-photon quantum ellipsometry without taking extraneous steps to calibrate both the source and/or detector(s) to obtain highly accurate ellipsometric measurements.

Figure 1:
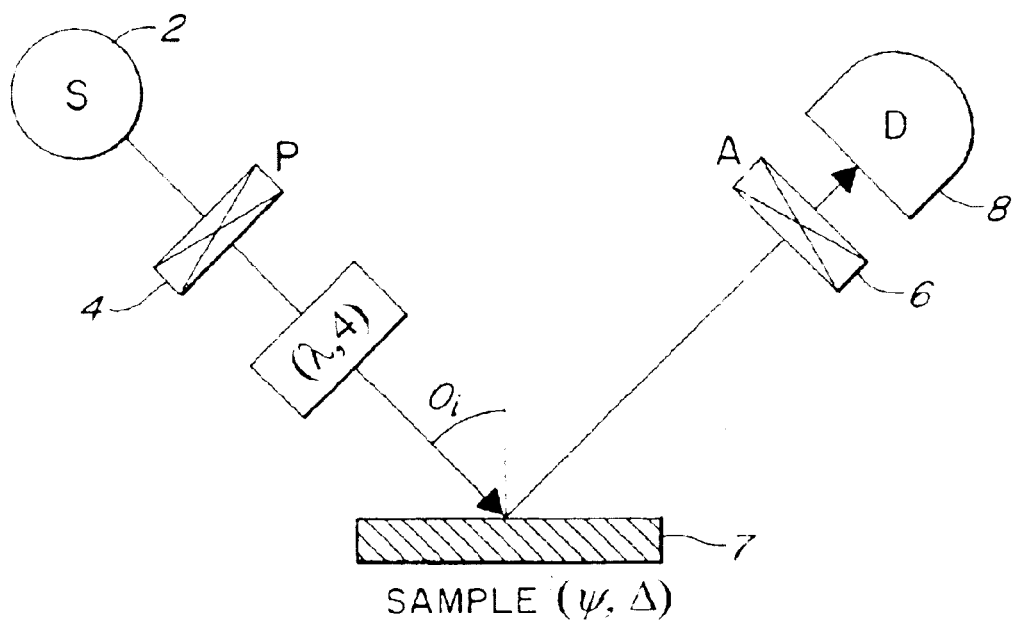
FIG. 1 illustrates a conventional null ellipsometer.
Figure 2:
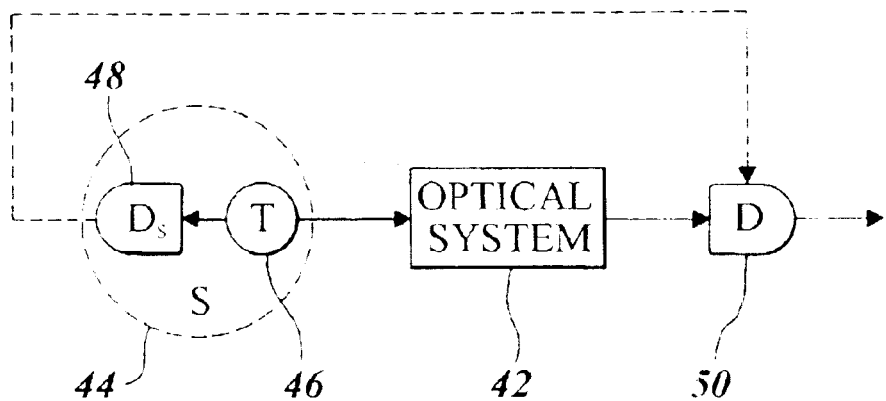
FIG. 2 illustrates a reliable single-photon source constructed from a twin-photon source and gated detector.

FIG. 2 illustrates a reliable single-photon source constructed from a twin-photon source and gated detector. A twin photon source 44 emits photons always in pairs. For purposes of illustration, the twin photons are emitted from two different directions. One of the photons is directed to a single-photon detector 48, and the other is directed into the optical system under test and then directed to the detector 50. The detection of a photon by detector 48 serves as a gate that activates 50. The arrival of the gating signal from detector 48 guarantees that a photon has entered the optical system 42 under test.

The twin-photon source 44 discussed may be readily realized via the process of spontaneous parametric down conversion (SPDC) from a second-order nonlinear crystal (NLC) when illuminated with a monochromatic laser beam (pump). A portion of the pump photons disintegrates into photon pairs. The photon pairs are highly correlated since they conserve the energy and momentum of the parent pump photon. Such an arrangement will be discussed more below.

Figure 3:
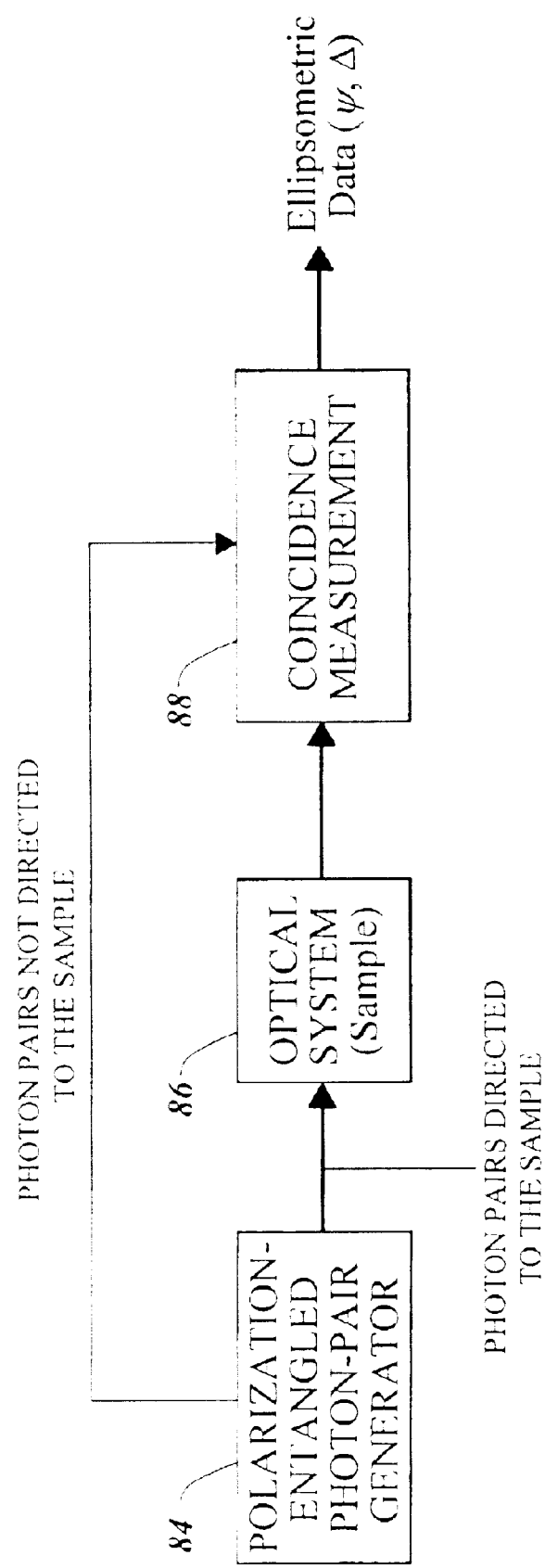
FIG. 3 illustrates a block diagram of the invention.

FIG. 3 illustrates a block diagram of the invention. The illustrative embodiment of the present invention is described by the polarization entangled photon pair generator 84, the optical sample 86, and coincidence measurement device 88. The polarization entangled photon-pair generator 84 provides the necessary components to produce entangled photon pairs. In particular, the polarization photon pair generator 84 includes an optical source of a monochromatic beam. The illustrative embodiment of the invention does not require that the light be ideal. The optical source may provide a pump beam, which is passed through a nonlinear optical medium. The source of the pump beam may be a laser, semiconductor laser, light-emitting diode, incandescent source, or other similar light source. The light source provides light in the form of a beam of photons. The light may be continuous-wave or pulses of, for example, femtosecond or longer duration. The light preferably has energy in the wavelength range from radiowaves to x-rays. The optical source may use twin beams of quantum-mechanically entangled photons, which exhibit photon-pair occurrence times that are highly, but not perfectly, correlated. Because energy is conserved in the entangled-pair creation process, the twin photons are produced nearly simultaneously and each has a wavelength longer than the original. Momentum is also conserved, resulting in a nearly one-to-one correspondence between the direction of travel of a photon in one beam and the direction of its matching photon in the other beam. The polarization photon pair generator 84 disintegrates the photons from the monochromatic beam to generate highly correlated photon pairs. These photon pairs are orthogonal to each other. Also, the polarization entangled photon-pair generator 84 directs one member of the photon pair to the optical sample 86 and the other member of the photon pair to the coincidence measurement device 88. Essentially, the polarization entangled photon-pair generator 84 acts like the twice source 40 mentioned above.

The nonlinear optical medium may be a crystal, a surface, an interface or other similar component. The nonlinear optical medium causes a portion of the pump beam to split into a signal beam and an idler beam (referred to collectively as twin beams), contributing a stream of daughter entangled photons to the signal beam and a corresponding stream of twin daughter entangled photons to the idler beam. The signal beam and idler beam may be referred to as entangled-photon beams (also called twin-photon, two-photon, or two-mode squeezed-state beams). The interaction of the pump beam with the nonlinear optical medium generates entangled-photon beams by means of a nonlinear optical process, such as spontaneous parametric downconversion as illustrated, or entangled-photon beams may be generated by other means.

Under the ideal spontaneous parametric downconversion (SPDC) each pump-beam photon is split into twin daughter photons which are emitted simultaneously. Since energy and momentum are conserved in the splitting process, the daughter photons share the energy and momentum of the mother. This entangles the directions of the two daughters so that the emission of one photon in a given direction is associated with an absolutely certain simultaneous emission of a twin photon in a matching direction. The twins may have the same frequency (wavelength or color), in which case they are identical (or degenerate); or differ in frequency (wavelength or color), in which case they are in a sense fraternal (or nondegenerate). The entanglement persists no matter how far away the photons might be from each other.

The beams may be generated by SPDC in poled or unpoled optical fibers, or at a surface or an interface, or directly at the source or surface of the device producing the pump beam. The beams may be generated by stimulated parametric downconversion or by cascaded atomic emissions, rather than by spontaneous parametric downconversion. With cascaded atomic emissions, a pump beam is incident on a material that emits a cascade of two or more photons, entangled via energy and momentum conservation.

Other nonlinear optical processes may be used to generate multiple entangled photons (three, four, and more) in multiple beams. Triples and quadruples of entangled photons are obtained from a higher-order downconverter, from a cascade of two-photon downconverters, or from atomic cascades (for example, an atom cascading through two intermediate levels to produce three entangled photons). Thus, multiphoton (e.g., three-photon) implementations of the invention are possible.

After the optical sample 86 receives the photons pairs by the polarization entangled photon-pair generator 84, these photon pairs are reflected and sent to the coincidence measuring device 88. The coincidence measuring device 88 calculates the coincidence of one of the photons of the photon pair reflected from the sample and the other of the photons of the photon pair. The coincidence measuring device 88 utilizes the entanglement properties of the reflections of the photon pairs directed to the sample and the photons pairs not directed to the sample and the calculated coincidence rate to obtain the various ellipsometric data. Thus, the invention does not require a reference sample to determine ellipsometric data.

The coincidence measure device 88 may include various polarization analyzers and detectors for measuring the coincidence rate. The polarization analyzers may be positioned at various angles.

The various embodiments of the invention discussed below include the three components 84, 86, and 88 of FIG. 3. There are many other specific arrangements that may be used to obtain ellipsometric data by utilizing entanglement of photon pairs without changing the scope of the invention.

Figure 4:
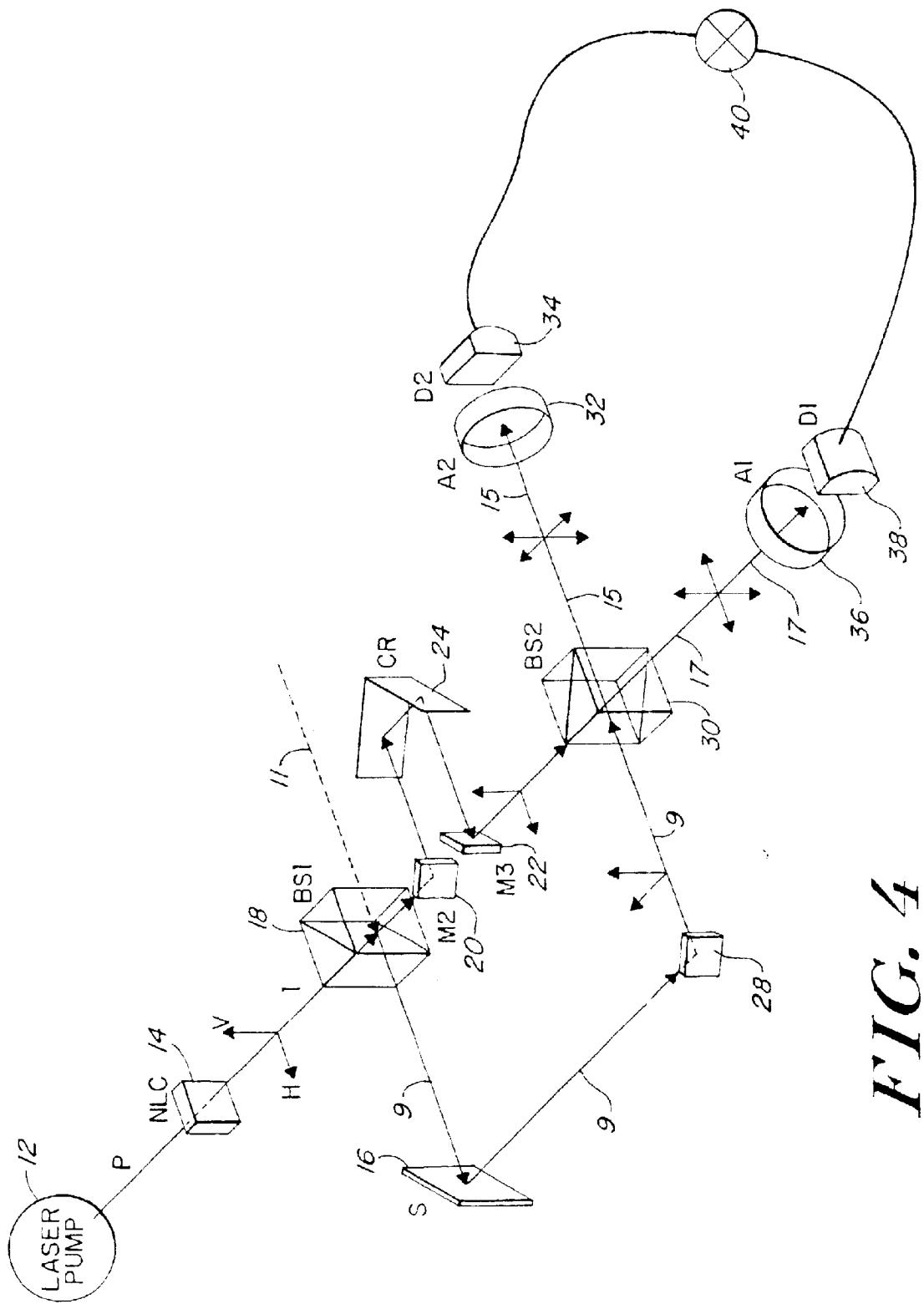
FIG. 4 illustrates a quantum ellipsometer using an entangled-photon hyper-interferometer.

FIG. 4 illustrates a quantum ellipsometer. This illustrative embodiment utilizes a nonlinear birefringent crystal (NLC) 14, which is illuminated by a laser pump 12, usually in the ultraviolet, whereby a pair of entangled photons H and V are generated by the process of the type-II spontaneous down conversion, as discussed above. Before the photons enter the first beam splitter 18, the photons are in a product polarization state, i.e., they exhibit classical correlations but not entanglement. At the first beam splitter 18 the photons are mixed with vacuum fluctuations entering the first beam splitter 18 via the empty port beam 11. Also, the first beam splitter 18 creates beams 13 and 9 where beam 9, is directed to a sample 16. The photons in beam 9 are reflected from the sample 16 and are then sent via a mirror 28 to a second beam splitter 30 where it is combined with beam 13. The path of lengths of beams 13 and 9 are adjusted to be equal by means of a delay line formed by mirrors, 20 and 22 and corner reflecting tube CR 21 place in beam 13. Beam splitter 30 splits the recombined beams 13 and 9 into beams 17 and 15. The linear polarizers 36 and 32 followed by single-photon detectors 38 and 34 then analyze beams 17 and 15. The polarization analyzers 36 and 32 are oriented at angles $\theta_1$ and $\theta_2$ with respect to V. The coincidence circuit 40 receives data from detectors 38 and 34 to calculate the coincidence rate. The configuration actually forms a hyper-interferometer, in which both the temporal aspect of the interference and the polarization entanglement properties of the photon pair are utilized.

As discussed above, the mixing of beams 13 and 9 in this embodiment leads to an auto-calibration feature of the hyper-interferometers. The nature of entanglement itself lends a self-referencing property that this illustrative embodiment exploits. The entangled photons in each pair reference each other as opposed to a laser, where the photons are independent. In a conventional ellipsometer, information about the sample is encoded in newly acquired properties of the beam and can be unraveled only by relying on another reference measurement in the absence of the sample. In the case of a beam of entangled photon pairs, measurements can be performed on the photon pair in coincidence, and the sample information encoded in the beam can be obtained by referencing one of the photons to the other. The photon-pairs are highly correlated since they conserve the energy and momentum of the parent pump photon 12, and they simultaneously are entangled in all their other defining parameters, such as frequency and polarization.

The mathematical description of the hyper-interferometer is best described in quantum mathematical terms, where the quantum-mechanical operators evolve through the system, while the quantum-mechanical state remains stationary. The signal and idler protons are represented by boson annihilation operators $\hat{a}_{s,V}$ and $\hat{a}_{i,H}$ where s and i refer to signal and idler photons, respectively, and V and H represent the two eigenpolarizations of the sample and the optical system. The sample is characterized by its complex coefficients for the V and H polarizations, $\tilde{r}_1$ and $\tilde{r}_2$ respectively. Using a symmetrical beam splitter model to represent first beam splitter 18, and second beam splitter 30, and the sample 16, it can be shown that the annihilation operator $\hat{a}_s$ representing beam 17, directly at the output of second beam splitter 30 is $$\hat{a}_5 = \frac{1}{2}\left\{(1+\tilde{r}_1)\hat{a}_{s,V} + (1-\tilde{r}_2)\hat{a}_{i,H}\right\}$$

and that the annihilation operator $\hat{a}_6$ representing beam 15 is $$\hat{a}_6 = \frac{j}{2}\left\{(1+\tilde{r}_1)\hat{a}_{s,V} + (1-\tilde{r}_2)\hat{a}_{i,H}\right\}.$$

It is important to note that the sample is illuminated by two independently polarized photons that are not in a 'superposition' state. With knowledge of the twin photon state generated by the nonlinear crystal one may predict average values of various measurable quantities according to the rules of quantum-mechanical theory.

For accurate ellipsometric measurements the measurable quantities used do not depend on the quantum efficiencies of the detectors 38 and 34. The most suitable quantity for this purpose is the coincidence count between the detector 38 and 34 calculated by the coincidence circuit 40. The coincidence count can be defined in terms of the boson creation and annihilation operators at the detectors, averaged over the quantum-mechanical state. The resulting expression for the coincidence count rate Nc, is given by $$Nc = C|\cos\theta_1\sin\theta_2(\tilde{r}_1+1)(\tilde{r}_2+1) - \sin\theta_1\cos\theta_2(\tilde{r}_1-1)(\tilde{r}_2-1)|^2, \qquad (1)$$

where C is a constant that depends on the physical parameters of the optical setup (including the quantum efficiencies of the detectors) and on the efficiency of the SPDC process. Equation 1 lends insight into the operation of this hyper-interferometer. There are four quantities that are mixed as result of the action of the two beam splitters 18 and 30: ($\tilde{r}_1 \pm 1$) and ($\tilde{r}_2 \pm 1$). This arises from the spatial-temporal component of the hyper-interferome. The weights of this mixture are determined by the rotation angles of the analyzers 36 and 32, which reside in the polarization component of the hyper-interferometer.

There are two special cases presented with this arrangement. In the first, the sample 16 is removed and replaced with an ideal mirror so that $\tilde{r}_1=-\tilde{r}_2=1$. The coincidence rate then becomes zero, irrespective of the analyzer angles. The beam splitters 18 and 30 combine the various probability amplitudes in such a way as to cancel out the possibility that two photons emerge from difference ports of the second beam splitter 30. Instead, they emerge from the same port, contributing to the rate of singles at the two detectors. This feature can be used as a test for the temporal alignment of the interferometer, to provide assurance that the signal and idler protons arrive at the detectors at the same time.

In the second case, the sample was removed from the hyper-interferometer or equivalently, insert a completely absorbing beam stop in the sample arm, whereupon $\tilde{r}_1=\tilde{r}_2=0$. In this case the coincidence rate becomes $$Nc = C\sin^2(\theta_1-\theta_2) \qquad (2)$$

which has been observed previously. This permits the proportionality constant C, which depends on the various parameters of the setup including the detector quantum efficiencies to be determined without having to resort to a reference sample. The ellipsometric data obtained from such a measurement is absolute, and not referenced to another sample as in the traditional practice of classical ellipsometry. The sample 16 is placed as indicated in FIG. 4 and the measurement is performed by recording the coincidence counts at the detectors for various angle settings of the polarization analyzers 36 and 32. Equation 2 can also be shown to yield three independent unknowns: the magnitudes of the two reflection coefficients and their relative phase. Three different angular settings of the pair of polarization analyzers suffice to obtain these parameters, but additional measurements with as many settings as the operator of this device wishes will reduce errors and enhance the accuracy of the measurements. The results of the measurements can be then used to estimate the optical properties of the sample as in traditional ellipsometry, but in an absolute way.

Although the quantum state emerging from the nonlinear crystal (NLC) 14 is not entangled, "effective" entanglement is obtained from post-selection measurements made in the coincidence scheme.

Other optical components, such as wave plates and polarization rotators, can be added to extend the measurement capability of our device into circular-polarized and other polarization entanglement bases. Further information about the sample can thus be obtained. The linear polarization analyzers 36 and 32, may be replaced by general polarization analyzers, i.e., analyzers that can be configured to detect any general polarization state. The setup can be easily adjusted to probe the sample tomographically by changing the delay in beam 13.

This embodiment can also be modified in various ways. One possible modification may be to add any additional optical components in both or either of the two arms of the Mach-Zender interferometer portion of the hyper-interferometer. Examples would be polarization manipulating devices, such as (polarization rotators, polarization analyzers, phase plates, polarization modulators, depolarizors, etc.) optical delays (polarization or non-polarization sensitive), or any other optical devices. The polarization interferometer portion of the hyper-interferometer can be modified by adding polarizing beam-splitters, phase-plates etc., to detect a general state of polarization and to set up a four-fold (or more) coincidence detection scheme. Optical delays (polarization or non-polarization sensitive) or polarization manipulating devices may be inserted in the path of the biphotons before the beam splitter.

Figure 5:
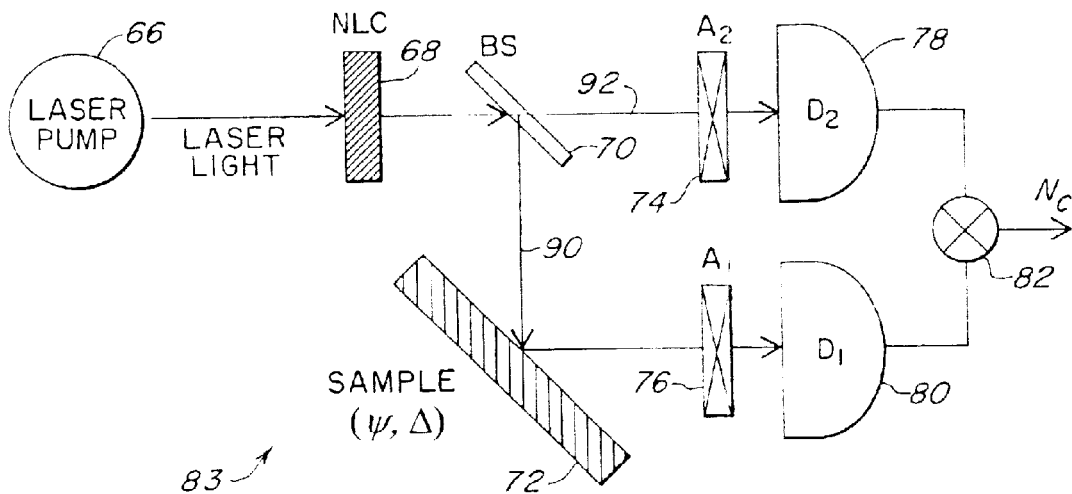
FIG. 5 illustrates an unentangled photon elliposometer.

FIG. 5 illustrates an unentangled photon ellipsometer. The unentangled photon ellipsometer 83 illustrates a collinear type-II SPDC in a standard twin-photon polarization interferometer. As discussed above, a NLC 68 is illuminated with a monochromatic laser pump 66. Portions of the pump photons disintegrate into photon pairs that are highly correlated since they conserve energy (frequency-matching) and momentum (phase-matching). Also, these photons have orthogonal polarizations. These photons emerge from the NLC 68 with a relative time delay due to the birefringence of the NLC 68. Passing the pair of photons through an appropriate birefringent material of suitable length compensates for this time delay. This temporal compensation is required for extracting $\psi$ and $\Delta$ from the measurements. The SPDC state is a polarization-product state $$|\psi\rangle = |HV\rangle. \tag{2}$$

Because the state is factorizable it is not entangled and the photons leave the NLC 68 in a collinear fashion. The twin photons which emerge from the NLC 68 with the state shown in relation 2, impinge on the input port of a non-polarizing beam splitter 70, so that the two photons are separated into the two output ports 90 and 92 of the beam splitter 70. Photons emerging from the output port 90 of the beam splitter 70 are directed to the sample 72 under test and are then directed to polarization analyzer 76 followed by single-photon detector 80. Photons emerging from the output port 92 are directed to polarization analyzer 74 followed by single-photon detector 78. A coincidence circuit 82 registers the coincidence rate $N_c$ of the detectors 78 and 80, which is proportional to the fourth-order coherence function of the fields at the detectors.

In this arrangement of the unentangled-photon ellipsometer 83, the coincidence is given by $$N_c = C[\tan^2\psi\cos^2\theta_1\sin^2\theta_2 + \tag{3}$$
$$\sin^2\theta_1\cos^2\theta_2 - 2\tan\psi\cos\Delta\cos\theta_1\cos\theta_2\sin\theta_1\sin\theta_2],$$

where the constant of proportionality C depends on the efficiencies of the detectors and duration of accumulation of coincidence. Plus, $\theta_1$ and $\theta_2$ are the angles of the axes of the analyzers 74 and 76 with respect to the horizontal directions. One can obtain C, $\psi$, and $\Delta$ with a minimum of three measurements with different analyzer settings, e.g. $\theta_2=0°$, $\theta_2=90°$, and $\theta_2=45°$, while $\theta_1$ remains fixed at any angle except 0° and 90°.

Although the quantum state emerging from the NLC 54 is not entangled, "effective" entanglement is obtained from post-selection measurements made in the coincidence scheme.

If the sample 72 is replaced by a perfect mirror, the coincidence rate in relation 3 becomes a sinusoidal pattern of 100% visibility, C sin² ($\theta_1-\theta_2$). The unentangled photon ellipsometer 83 makes use of simultaneous emitted photon pairs, which removes the need for a reference sample.

Figure 6:
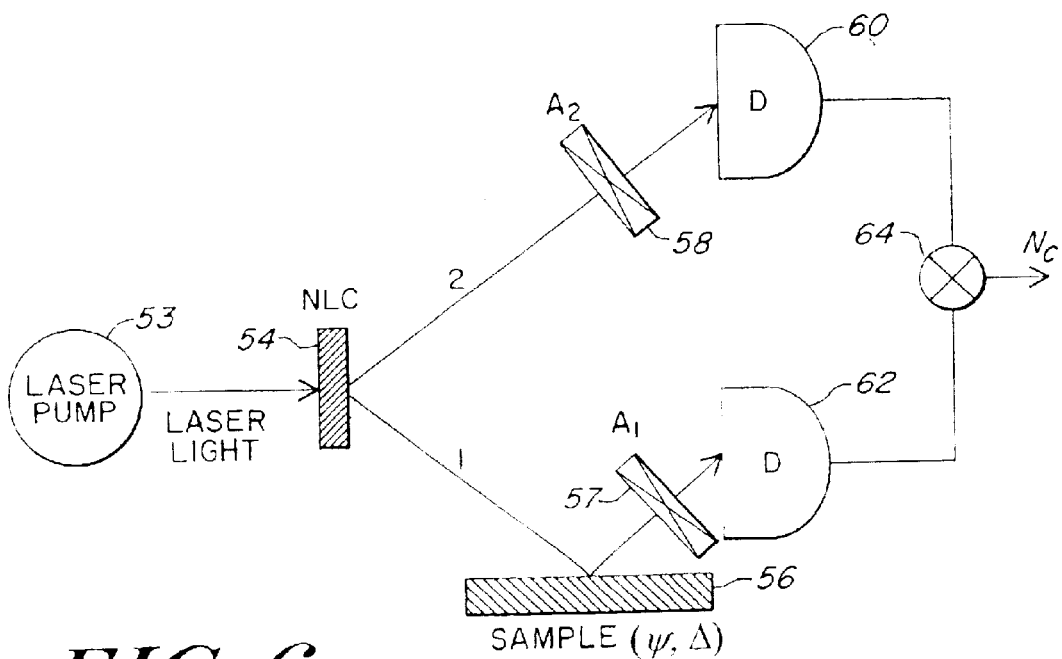
FIG. 6 illustrates an entangled photon ellipsometer.

FIG. 6 illustrates an entangled photon ellipsometer. The ellipsometer illustrated in FIG. 6 is but the simplest setup envisioned that makes use of the rich entanglement properties of the photon pairs. FIG. 6 is the preferred embodiment of the present invention.

The twin-photon source 40 discussed may be readily realized via the process of spontaneous parametric down conversion (SPDC) from a second-order nonlinear crystal (NLC) 54 when illuminated with a monochromatic laser beam (pump) 53. A portion of the pump photons disintegrates into photon pairs. The two photons are known as the signal and the idler. They are highly correlated since they conserve the energy and momentum of the parent pump photon, and they are simultaneously entangled in all their other defining parameters, such as frequency and polarization.

The signal and idler photons have orthogonal polarizations, one extraordinary and the other ordinary. These two photons emerge from the NLC 54 with a relative time delay due to the birefringence of the NLC 54. In this arrangement, the need for a beam splitter has been eliminated. The NLC 54 is adjusted to produce a SPDC in a type-II noncollinear configuration as shown in FIG. 6. The signal and idler photons are emitted in a polarization-entangled state described by $$|\Psi\rangle = \frac{1}{\sqrt{2}}(|HV\rangle + |VH\rangle) \tag{4}$$

Although the two-photon entangled state is a pure quantum state the signal and idler photons considered separately are each unpolarized. The signal photon enters the linear polarization analyzer 58 followed by detector 60. The idler photon is directed into the sample 56 and enters the linear polarization analyzer 57 followed by detector 62. A coincidence circuit 64 registers the coincidence rate Nc of the detectors 62 and 60.

In this arrangement of the entangled-photon ellipsometer, the coincidence is given by $$N_c = C|\beta e^{j\Delta}\cos\theta_1\sin\theta_2 + \sin\theta_1\cos\theta_2|^2 \propto \tag{5}$$
$$C[\beta^2\cos^2\theta_1\sin^2\theta_2 + \sin^2\theta_1\cos^2\theta_2 + 2\beta\cos\Delta\cos\theta_2\sin\theta_1\sin\theta_2].$$

Here C is a constant that includes the quantum efficiency of the detectors 38 and 34 and the various parameters of the experimental arrangement, $\beta=\sqrt{\tan\psi}$, and $\theta_1$ and $\theta_2$ is the angle of analyzers 36 and 32 respectively with respect to H. If the sample is replaced with a perfect mirror the coincidence rate is a sinusoidal pattern of 100% visibility. In practice, by judicious control of the apertures placed in the downconverted beams, visibilities close to 100% can be obtained.

One may use the relation (5) to extract ellipsometric data by fixing one of the analyzers and rotating the other. It is advantageous to fix analyzer 38 and rotate analyzer 32. One may choose $\theta_2=45°$, for example, whereupon $$N_c = \left(\frac{C}{2}|\beta e^{j\Delta}\cos\theta_1 + \sin\theta_1|^2\right). \quad (6)$$

Three angles of analyzer 36 are sufficient for estimating the three parameters C, $\psi$, and $\Delta$ (an obvious chooses would be $\theta_1=0°$, 45°, and 90°. It is sometime advantageous to choose a different value of $\theta_2$ to equalize the two terms in the first line of relation (5), particularly if $\beta\gg1$ or $\beta\ll1$.

An important feature of this embodiment is that it is not sensitive to an overall mismatch in the length of the two arms of the setup. In this case one can show that the coincidence rate is identical to that given in relation (5), regardless of the mismatch.

An advantage of this setup over the ellipsometric counterpart, is that the two arms of the ellipsometer are separate and light beams traverse them independently in different directions. This allows various instrumentation errors of the classical setup to be circumvented. For example, placing optical elements before the sample causes beam deviation errors when the faces of the optical components are not exactly parallel. This leads to an error in the angle of incidence and, consequently, errors in the estimated parameters of the sample. In the invention there are no optical components placed between the source (NLC) 54 and the sample 56. Any desired polarization manipulation may be performed in the other arm of the entangled two-photon ellipsometer.

Also, in an entangled twin-photon ellipsometer the polarization of the incoming light is dictated by the phase matching conditions of the nonlinear interaction in the NLC 54. The polarization defined in classical ellipsometry. The NLC 54 is aligned for type-II SPDC so that only one polarization component of the pump generates SPDC, whereas the orthogonal component of the pump 53 does not since it does not satisfy the phase-matching conditions. The advantage is the downconversion process assures the stability of polarization along a particular direction.

Also, this embodiment may utilize other entangle-pairs, such as electrons, electron positron pairs, atoms, molecules, or other coupled entities.

Although the present invention has been shown and described with respect to several preferred embodiments thereof, various changes, omissions and additions to the form and detail thereof, may be made therein, without departing from the spirit and scope of the invention.

What is claimed is:

1. A system for measuring ellipsometric data from a sample, comprising:
   a source for providing a monochromatic light beam;
   a nonlinear crystal for converting the monochromatic light beam into photon pairs by disintegrating photons from the monochromatic light beam, such that each of the photon pairs exhibits entanglement properties, wherein one of the photons of the pair is directed to the sample and the other of the photons of the pair is not directed to the sample; and
   a circuit for calculating a coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

2. The system of claim 1, wherein the photon pair are highly correlated and conserve energy and momentum of the source.

3. The system of claim 1 further comprising a second polarizing component for receiving and analyzing the polarization of said other of said photon pair and directing said other of said photon pair to a second detector.

4. The system of claim 3, wherein said nonlinear crystal is adjusted to produce a in a spontaneous parametric downconversion in a type II non-collinear configuration.

5. The system of claim 4 further comprising a first polarizing component for receiving and analyzing the polarization of said one of said photon pair reflected from said sample and directing said reflections from said sample of said one of said photon pair to a first detector.

6. The system of claim 5, wherein said source is a laser pump.

7. A method of measuring ellipsometric data from a sample, comprising:
   providing a monochromatic light beam;
   converting the monochromatic light beam into photon pairs by disintegrating photons from the monochromatic light beam, such that each of the photon pairs exhibits entanglement properties, wherein one of the photons of the pair is directed to the sample and the other of the photons of the pair is not directed to the sample; and
   calculating the coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

8. The method of claim 7, wherein the photons pairs are highly correlated and conserve energy and momentum of the source.

9. The method of claim 8 further comprising analyzing the polarization of said reflections from said sample of said one of said photon pairs.

10. The method of claim 1 further comprising analyzing the polarization of said other of the photons of said photon pair.

11. The method of claim 10, wherein said source is a laser pump.

12. A system for measuring ellipsometric data from a sample, comprising:
    a source for providing a monochromatic light beam;
    a nonlinear crystal converting the monochromatic light beam into photon pairs and creating a first beam that includes photon-pairs from disintegrated photons from said monochromatic beam,
    a first beam splitter for splitting the first beam into a second beam and third beam, wherein said second beam includes photons from said photon-pairs directed to the sample and said third beam includes photons from said photon-pairs not directed to said sample,
    a second beam splitter for combining reflected photons from said sample of said second beam and third beam into a recombined beam and splitting said recombined beam into a fourth and fifth beam, and
    a coincidence circuit for calculating the coincidence of the fourth and fifth beam, wherein measurements on said sample are obtained by analyzing the coincidence and entanglement properties of said photons in said fourth and fifth beam.

13. The system of claim 12, wherein the photons pairs are highly correlated and conserve energy and momentum of the source.

14. The system of claim 12 further comprising a second polarizing component for receiving and analyzing said fourth beam and directing said fourth beam to a second detector.

15. The system of claim 14 further comprising a first polarizing component for receiving and analyzing said fifth beam and directing said fifth beam to a first detector.

16. The system of claim 17, wherein the source is a laser pump.

17. A system for measuring ellipsometric data from a sample, comprising:
   a source for providing a monochromatic light beam;
   a nonlinear crystal converting the monochromatic light beam into photon pairs and creating a first beam that includes photon-pairs from disintegrated photons from said monochromatic beam,
   a first beam splitter for splitting the first beam into a second beam and third beam, wherein said second beam includes photons from said photon-pairs directed to the sample and said third beam includes photons from said photon-pairs not directed to said sample, and
   a coincidence circuit for calculating the coincidence of reflections from said sample of said second beam and third beam, wherein measurements on said sample are obtained by analyzing the coincidence and entanglement properties of said photon-pairs between said reflections from said sample of said second beam and third beam.

18. The system of claim 17, wherein the photons pairs are highly correlated and conserve energy and momentum of the source.

19. The system of claim 17 further comprising a second polarizing component for receiving and analyzing said third beam and directing said third beam to a second detector.

20. The system of claim 19 further comprising a first polarizing component for receiving and analyzing said reflections from said sample of said second beam and directing said reflections from said sample of said second beam to a first detector.

21. The system of claim 17, wherein the source is a laser pump.

22. The system of claim 17, wherein said NLC is adjusted to be in a spontaneous parametric downconversion in a type II collinear configuration.

23. A method of measuring ellipsometric data from a sample, comprising:
   providing a monochromatic light beam;
   converting the monochromatic light beam into photon pairs and creating a first beam that includes photon-pairs from disintegrated photons from said monochromatic beam,
   splitting said first beam into a second beam and third beam, wherein said second beam includes photons from said photon-pairs directed to the sample and said third beam includes photons from said photon-pairs not directed to said sample, and
   calculating the coincidence of reflections from said sample of said second and third beam, wherein measurements on said sample are obtained by analyzing the coincidence and entanglement properties of said photon-pairs between said reflections from said second beam and third beam.

24. The method of claim 23, wherein the photons pairs are highly correlated and conserve energy and momentum of the source.

25. The method of claim 23 further comprising receiving and analyzing polarizations of said third beam.

26. The method of claim 25 further comprising receiving and analyzing polarizations of said reflections from said sample of said second beam.

27. The method of claim 23, wherein the source is a laser pump.

28. The method of claim 23, wherein said NLC is adjusted to be in a spontaneous parametric downconversion in a type II collinear configuration.

29. A method of measuring ellipsometric data from a sample, comprising:
   providing a monochromatic light beam;
   converting the monochromatic light beam into photon pairs and creating a first beam that includes photon-pairs from disintegrated photons from said monochromatic beam,
   splitting the first beam into a second beam and third beam, wherein said second beam includes photons from said photon-pairs directed to the sample and said third beam includes photons from said photon-pairs not directed to said sample,
   combining reflections from said sample of said second beam and third beam into a recombined beam and splitting said recombined beam into a fourth and fifth beam, and
   calculating the coincidence of the fourth and fifth beam, wherein measurements on said sample are obtained by analyzing the coincidence and entanglement properties of said photons in said fourth and fifth beam.

30. The method of claim 29, wherein the photons pairs are highly correlated and conserve energy and momentum of the source.

31. The method of claim 29 further comprising receiving and analyzing said fourth beam and directing said fourth beam to a second detector.

32. The method of claim 31 further comprising receiving and analyzing said fifth beam and directing said fifth beam to a first detector.

33. The method of claim 29, wherein the source is a laser pump.

34. A system for measuring ellipsometric data from a sample, comprising:
   an entangled photon-pair generator for converting a monochromatic light beam into photon pairs, such that one of the photons of the pair is directed to the sample and the other of the photons of the pair is not directed to the sample, and
   a coincidence measuring device for calculating a coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

35. The system of claim 34, wherein the generator uses an atomic cascade process to generate entangled photon pairs.

36. The system of claim 34, wherein the generator uses a nonlinear crystal (NLC) to generate entangled photon pairs.

37. The system of claim 36, wherein said nonlinear crystal is adjusted to be in a spontaneous parametric downconversion in a type II non-collinear configuration.

38. The system of claim 37 further comprising a second polarizing component for receiving and analyzing the polarization of said other of said photon pairs.

39. The system of claim 38 further comprising a first polarizing component for receiving and analyzing the polarization of said reflections from said sample of one of said photon pairs.

40. The system of claim 36, wherein said nonlinear crystal is adjusted to be in a spontaneous parametric downconversion in a type II collinear configuration.

41. The system of claim 40 further comprising a second polarizing component for receiving and analyzing the polarization of said other of said photon pairs.

42. The system of claim 41 further comprising a first polarizing component for receiving and analyzing the polarization of said one of the photons of the photon pair reflected from the sample.

43. The system of claim 42, wherein the entanglement properties of said one of the photons of the photon pair reflected from the sample and the other of the photons of the photon pair are obtained from post selection measurements made in said coincidence measuring device.

44. The system of claim 34, wherein said source is a laser pump.

45. The system of claim 34, wherein said source is a light emitting diode.

46. The system of claim 34, wherein said source is an incandescent source.

47. The system of claim 34, wherein the entangled photon-pair generator uses a SPDC in poled or unpoled optical fibers to generate photon pairs at a surface of said of source.

48. The system of claim 34, wherein the entangled photon-pair generator uses stimulated spontaneous parametric downconversion to generate photon pairs.

49. The system of claim 34, wherein the entangled photon-pair generator uses a cascade of two photon downconverters to generate multiple photon pairs.

50. The system of claim 34, wherein the entangled photon-pair generator uses atomic cascades to generate multiple photon pairs.

51. A method of measuring ellipsometric data from a sample, comprising:
   converting a monochromatic light beam into photon pairs, such that one of the photons of the pair is directed to the sample and the other of the photons of the pair is not directed to the sample, and
   calculating a coincidence of one of the photons of the photon pair reflected from the sample and the other of the photons of the photon pair, wherein the measurements of the sample are obtained by analyzing the coincidence and the entanglement properties between one of the photons of the photon pair reflected from the sample and the other of the photons of the photon pair.

52. The method of claim 51, wherein generating photon pairs further comprises utilizing an atomic cascade process to generate entangled photon pairs.

53. The method of claim 51, wherein generating photon pairs further comprises utilizing a nonlinear crystal (NLC) to generate entangled photon pairs.

54. The method of claim 53, wherein said nonlinear crystal is adjusted to be in a spontaneous parametric downconversion in a type II non-collinear configuration.

55. The method of claim 54 further comprising receiving and analyzing the polarization of said other of said photon pairs.

56. The method of claim 55 further comprising receiving and analyzing the polarization of said reflections from said sample of one of said photon pairs.

57. The method of claim 56, wherein said nonlinear crystal is adjusted to be in a spontaneous parametric downconversion in a type II collinear configuration.

58. The method of claim 57 further comprising receiving and analyzing the polarization of said other of said photon pairs.

59. The method of claim 58 further comprising receiving and analyzing the polarization of said one of the photons of the photon pair reflected from the sample.

60. The method of claim 57, wherein the entanglement properties of said one of the photons of the photon pair reflected from the sample and the other of the photons of the photon pair are obtained from post selection measurements made in said coincidence measuring device.

61. The method of claim 53, wherein said source is a laser pump.

62. The method of claim 53, wherein said source is a light emitting diode.

63. The method of claim 53, wherein said source is an incandescent source.

64. The method of claim 53, wherein the entangled photon-pair generator uses a SPDC in poled or unpoled optical fibers to generate photon pairs at a surface of said of source.

65. The method of claim 53, wherein the entangled photon-pair generator uses stimulated spontaneous parametric downconversion to generate photon pairs.

66. The method of claim 53, wherein the entangled photon-pair generator uses a cascade of two photon downconverters to generate multiple photon pairs.

67. The method of claim 53, wherein the entangled photon-pair generator uses atomic cascades to generate multiple photon pairs.

* * * * *